(12) United States Patent
Ogasawara et al.

(10) Patent No.: US 7,527,878 B2
(45) Date of Patent: May 5, 2009

(54) ORGANIC ELECTROLUMINESCENCE ELEMENT AND SILICON COMPOUND

(75) Inventors: Jun Ogasawara, Minami-ashigara (JP); Saisuke Watanabe, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 377 days.

(21) Appl. No.: 11/085,223

(22) Filed: Mar. 22, 2005

(65) Prior Publication Data

US 2005/0214572 A1    Sep. 29, 2005

(30) Foreign Application Priority Data

Mar. 26, 2004 (JP) .............................. 2004-091895

(51) Int. Cl.
*H01L 51/54* (2006.01)
*C09K 11/06* (2006.01)
*C07F 7/10* (2006.01)

(52) U.S. Cl. ................... 428/690; 428/917; 313/504; 313/506; 257/40; 257/E51.046; 257/E51.05; 548/440; 556/413; 540/587; 540/588

(58) Field of Classification Search ............... 428/690, 428/917; 313/502–509; 427/58, 66; 252/301.16–301.35; 257/E51.001–E51.052

See application file for complete search history.

(56) References Cited

U.S. PATENT DOCUMENTS

| | | | |
|---|---|---|---|
| 6,310,231 B1 * | 10/2001 | Igarashi et al. | ............... 556/489 |
| 7,011,871 B2 * | 3/2006 | Herron et al. | ................ 428/1.4 |
| 2002/0028329 A1 * | 3/2002 | Ise et al. | ..................... 428/336 |
| 2005/0064238 A1 * | 3/2005 | Lee et al. | ................... 428/690 |

FOREIGN PATENT DOCUMENTS

JP        2000-351966 A        12/2000

* cited by examiner

Primary Examiner—Marie R. Yamnitzky
(74) Attorney, Agent, or Firm—Birch, Stewart, Kolasch & Birch, LLP

(57) ABSTRACT

An organic electroluminescence element, which contains at least one organic layer that includes a luminescent layer between a pair of electrodes, wherein the organic layer contains at least one compound represented by formula (1):

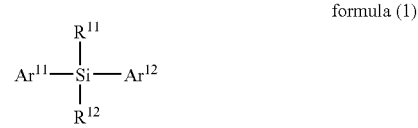

formula (1)

wherein $R^{11}$ and $R^{12}$ each independently represent an aryl or heteroaryl group; when $R^{11}$ or $R^{12}$ is a phenyl group, it has no nitrogen-containing heterocyclic group on $R^{11}$ or $R^{12}$ as a substituent; $Ar^{11}$ and $Ar^{12}$ each independently represent a group represented by formula (2):

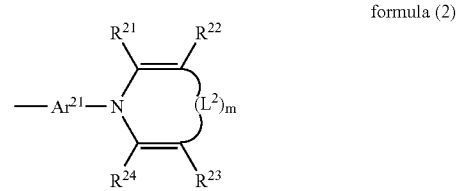

formula (2)

wherein $Ar^{21}$ represents an arylene or heteroarylene group; $R^{21}$, $R^{22}$, $R^{23}$, and $R^{24}$ each independently represent a substituent or a hydrogen atom; $L^2$ represents a substituted or unsubstituted o-arylene or vinylene group, —NR— (R represents a substituent), —O—, or —S—; and m is 0 or 1.

7 Claims, No Drawings

ORGANIC ELECTROLUMINESCENCE ELEMENT AND SILICON COMPOUND

FIELD OF THE INVENTION

The present invention relates to an organic electroluminescence element capable of converting electric energy to light, so as to emit light.

BACKGROUND OF THE INVENTION

Today active research and development are carried out on various display elements. Of the elements, organic electroluminescence (EL) elements (hereinafter, referred to as EL elements, luminescence elements, or the luminescence elements of the present invention) can give luminescence having high brightness at low voltage, and therefore attention is paid to the elements as promising display devices.

To improve element-endurance, JP-A-2000-351966 ("JP-A" means unexamined published Japanese patent application) suggests specific silane compounds and light emitting elements containing one or more thereof. This publication discloses (4-25), (4-26), (4-27), and (4-28). However, in respect to these compounds, there has been a need for the endurance of the element to be further improved.

SUMMARY OF THE INVENTION

The present invention resides in an organic electroluminescence element, which comprises at least one organic layer that includes a luminescent layer between a pair of electrodes, wherein the organic layer contains a silicon compound represented by formula (1):

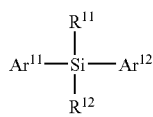

formula (1)

wherein $R^{11}$ and $R^{12}$ each independently represent an aryl or heteroaryl group; when $R^{11}$ or $R^{12}$ is a phenyl group, it has no nitrogen-containing heterocyclic group on $R^{11}$ or $R^{12}$ as a substituent; $Ar^{11}$ and $Ar^{12}$ each independently represent a group represented by formula (2):

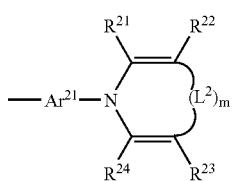

formula (2)

wherein $Ar^{21}$ represents an arylene or heteroarylene group; $R^{21}$, $R^{22}$, $R^{23}$, and $R^{24}$ each independently represent a substituent or a hydrogen atom; $L^2$ represents a substituted or unsubstituted o-arylene or vinylene group, —NR— (R represents a substituent), —O—, or —S—; and m is 0 or 1.

Further, the present invention resides in a silicon compound represented by formula (3) or (4):

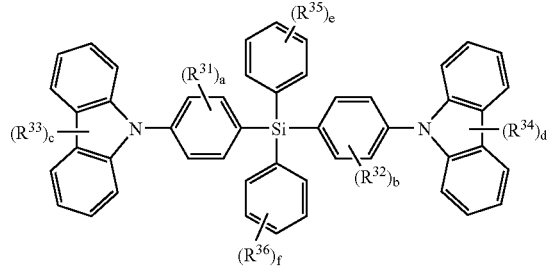

formula (3)

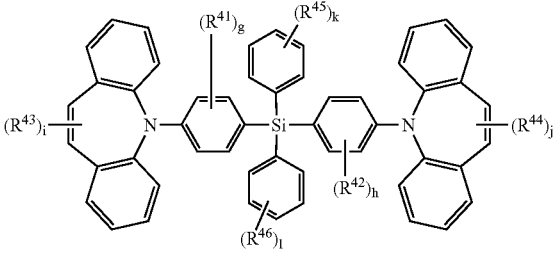

formula (4)

wherein $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represent an alkyl group, an aryl group, or a substituent bonding with each other to form an aromatic ring, a, b, g, and h each independently represent an integer of from 0 to 4; c and d each independently represent an integer of from 0 to 8; i and j each independently represent an integer of from 0 to 2; and e, f, k, and l each independently represent an integer of from 0 to 5.

Other and further features and advantages of the invention will appear more fully from the following description.

DETAILED DESCRIPTION OF THE INVENTION

According to the present invention, there is provided the following means:

(1) An organic electroluminescence element, comprising at least one organic layer that includes a luminescent layer between a pair of electrodes, wherein the organic layer contains at least one compound represented by formula (1):

formula (1)

wherein $R^{11}$ and $R^{12}$ each independently represent an aryl or heteroaryl group; when $R^{11}$ or $R^{12}$ is a phenyl group, it has no nitrogen-containing heterocyclic group on $R^{11}$ or $R^{12}$ as a substituent; $Ar^{11}$ and $Ar^{12}$ each independently represent a group represented by formula (2):

formula (2)

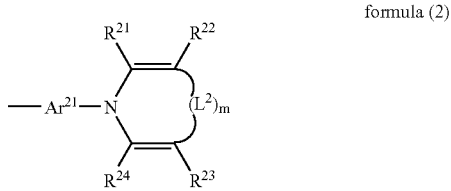

wherein $Ar^{21}$ represents an arylene or heteroarylene group; $R^{21}$, $R^{22}$, $R^{23}$, and $R^{24}$ each independently represent a substituent or a hydrogen atom; $L^2$ represents a substituted or unsubstituted o-arylene or vinylene group, —NR— (R represents a substituent), —O—, or —S—; and m is 0 or 1.

(2) The organic electroluminescence element according to (1), wherein m in formula (2) is 0.

(3) The organic electroluminescence element according to (1), wherein m in formula (2) is 1, and wherein $L^2$ is substituted or a unsubstituted o-arylene or vinylene group.

(4) The organic electroluminescence element according to (1), wherein $R^{11}$ and $R^{12}$ in formula (1) are each independently an unsubstituted aryl group, or an unsubstituted heteroaryl group.

(5) The organic electroluminescence element according to (4), wherein m in formula (2) is 0.

(6) The organic electroluminescence element according to (4), wherein m in formula (2) is 1, and wherein $L^2$ is a substituted or unsubstituted o-arylene or vinylene group.

(7) The organic electroluminescence element according to (1), wherein the compound represented by formula (1) is a compound represented by formula (3) or (4):

formula (3)

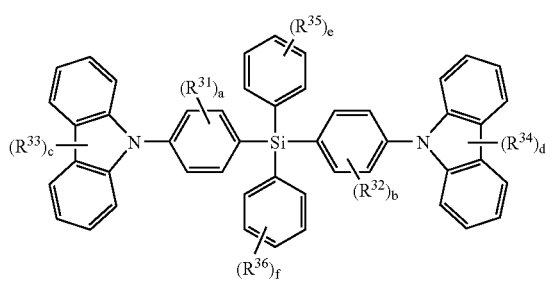

formula (4)

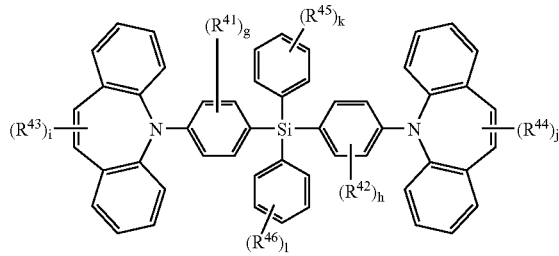

wherein $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represent an alkyl group, an aryl group, or a substituent bonding with each other to form an aromatic ring; a, b, g, and h each independently represent an integer of from 0 to 4; c and d each independently represent an integer of from 0 to 8; i and j each independently represent an integer of from 0 to 2; and e, f, k, and l each independently represent an integer of from 0 to 5.

(8) The organic electroluminescence element according to (7), wherein the compound represented by formula (1) is a compound represented by formula (3), wherein $R^{31}$, $R^{32}$, $R^{33}$, $R^{34}$, $R^{35}$, and $R^{36}$ each independently represent an aryl group; c and d each independently represent an integer of from 0 to 4; and a, b, e and f each independently represent an integer of 0 or 1.

(9) The organic electroluminescence element according to (7), wherein the compound represented by formula (1) is a compound represented by formula (4), wherein $R^{41}$, $R^{42}$, $R^{45}$, and $R^{46}$ each independently represent an aryl group; $R^{43}$ and $R^{44}$ each independently represent a substituent bonding with each other to form an aromatic ring; i and j each independently represent an integer of from 1 or 2; and g, h, k and l each independently represent an integer of 0 or 1.

(10) A compound represented by formula (3) or (4):

formula (3)

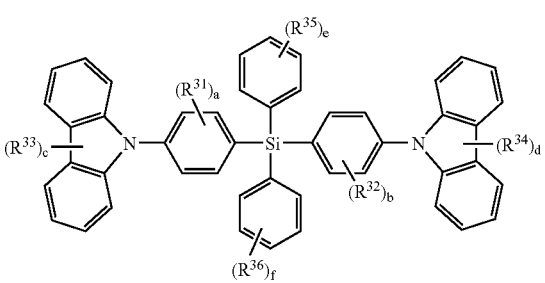

formula (4)

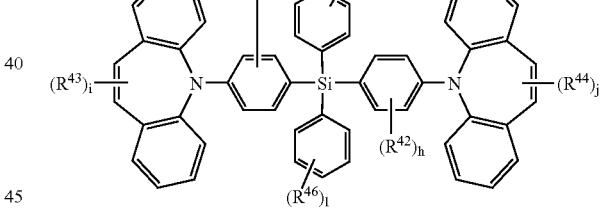

wherein $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represent an alkyl group, an aryl group, or a substituent bonding with each other to form an aromatic ring; a, b, g, and h each independently represent an integer of from 0 to 4; c and d each independently represent an integer of from 0 to 8; i and j each independently represent an integer of from 0 to 2; and e, f, k, and l each independently represent an integer of from 0 to 5.

(11) The compound according to (10), wherein the compound is a compound represented by formula (3), wherein $R^{31}$, $R^{32}$, $R^{33}$, $R^{34}$, $R^{35}$, and $R^{36}$ each independently represent an aryl group; c and d each independently represent an integer of from 0 to 4; and a, b, e and f each independently represent an integer of 0 or 1.

(12) The compound according to (10), wherein the compound is a compound represented by formula (4), wherein $R^{41}$, $R^{42}$, $R^{45}$, and $R^{46}$ each independently represent an aryl group; $R^{43}$ and $R^{44}$ each independently represent a substituent bonding with each other to form an aromatic ring;

i and j each independently represent an integer of from 1 or 2; and g, h, k, and l each independently represent an integer of 0 or 1.

A preferred embodiment of the present invention is an organic electroluminescence element comprising one or more organic layers that include a luminescent layer between a pair of electrodes, wherein the organic layer(s) contain(s) at least one compound represented by formula (1):

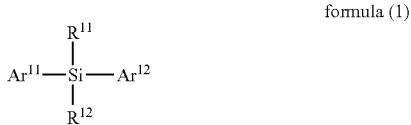

formula (1)

wherein $R^{11}$ and $R^{12}$ each independently represent an aryl or heteroaryl group; when $R^{11}$ or $R^{12}$ is a phenyl group, there is no nitrogen-containing heterocyclic group on $R^{11}$ or $R^{12}$ as a substituent; $Ar^{11}$ and $Ar^{12}$ each independently represent a group represented by formula (2):

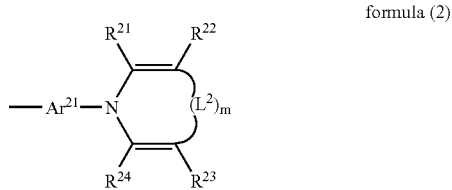

formula (2)

wherein $Ar^{21}$ represents an arylene or heteroarylene group; $R^{21}$, $R^{22}$, $R^{23}$, and $R^{24}$ each independently represent a substituent or a hydrogen atom; $L^2$ represents substituted or unsubstituted o-arylene, vinylene, —NR— (R represents a substituent), —O—, or —S—; and m is 0 or 1.

The following describes formula (1). $R^{11}$ and $R^{12}$ each independently represent an aryl or heteroaryl group. $R^{11}$ and $R^{12}$ are each preferably a monocyclic, bicyclic, or tricyclic aryl group or heteroaryl group, more preferably a phenyl, naphthyl, pyridyl, or carbazolyl group, and most preferably a phenyl group. $R^{11}$ and $R^{12}$ may each have a substituent. When $R^{11}$ or $R^{12}$ is a phenyl group, there is no nitrogen-containing heterocyclic group on $R^{11}$ or $R^{12}$ as a substituent (i.e. when $R^{11}$ and/or $R^{12}$ is phenyl group, $R^{11}$ and/or $R^{12}$ has no nitrogen-containing heterocyclic group on them as a substituent.). The substituent may be preferably any one of the following substituents A.

(Substituent A)

Examples of the substituents A include an alkyl group (preferably an alkyl group having 1 to 30 carbon atoms, more preferably 1 to 20 carbon atoms, and most preferably 1 to 10 carbon atoms, e.g., methyl, ethyl, iso-propyl, tert-butyl, n-octyl, n-decyl, n-hexadecyl, cyclopropyl, cyclopentyl, cyclohexyl), an alkenyl group (preferably an alkenyl group having 2 to 30 carbon atoms, more preferably 2 to 20 carbon atoms, and most preferably 2 to 10 carbon atoms, e.g., vinyl, allyl, 2-butenyl, 3-pentenyl), an alkynyl group (preferably an alkynyl group having 2 to 30 carbon atoms, more preferably 2 to 20 carbon atoms, and most preferably 2 to 10 carbon atoms, e.g., propargyl, 3-pentynyl), an aryl group (preferably an aryl group having 6 to 30 carbon atoms, more preferably 6 to 20 carbon atoms, and most preferably 6 to 12 carbon atoms, e.g., phenyl, p-methylphenyl, naphthyl, anthranyl), an amino group (preferably an amino group having 0 to 30 carbon atoms, more preferably 0 to 20 carbon atoms, most preferably 0 to 10 carbon atoms, e.g., amino, methylamino, dimethylamino, diethylamino, dibenzylamino, diphenylamino, ditolylamno), an alkoxy group (preferably an alkoxy group having 1 to 30 carbon atoms, more preferably 1 to 20 carbon atoms, most preferably 1 to 10 carbon atoms, e.g., methoxy, ethoxy, butoxy or 2-ethylhexyloxy), an aryloxy group (preferably an aryloxy having 6 to 30 carbon atoms, more preferably 6 to 20 carbon atoms, most preferably 6 to 12 carbon atoms, e.g., phenyloxy, 1-naphthyloxy, 2-naphthyloxy), a heteroaryloxy group (a heteroaryloxy group having preferably 1 to 30 carbon atoms, more preferably 1 to 20 carbon atoms, most preferably 1 to 12 carbon atoms, e.g., pyridyloxy, pyrazyloxy, pyrimidyloxy, quinolyloxy), an acyl group (preferably an acyl group having 1 to 30 carbon atoms, more preferably 1 to 20 carbon atoms, most preferably 1 to 12 carbon atoms, e.g., acetyl, benzoyl, formyl, pivaloyl), an alkoxycarbonyl group (preferably an alkoxycarbonyl group having 2 to 30 carbon atoms, more preferably 2 to 20 carbon atoms, most preferably 2 to 12 carbon atoms, e.g., methoxycarbonyl or ethoxycarbonyl), an aryloxycarbonyl group (preferably aryloxycarbonyl group having 7 to 30 carbon atoms, more preferably 7 to 20 carbon atoms, most preferably 7 to 12 carbon atoms, e.g., phenyloxycarbonyl), an acyloxy group having 2 to 30 carbon atoms, more preferably 2 to 20 carbon atoms, and most preferably 2 to 10 carbon atoms, e.g., acetoxy, benzoyloxy), an acylamino group (preferably an acylamino group having 2 to 30 carbon atoms, more preferably 2 to 20 carbon atoms, and most preferably 2 to 10 carbon atoms, e.g., acetylamino, benzoylamino), an alkoxycarbonylamino group (preferably an alkoxycarbonylamino group having 2 to 30 carbon atoms, more preferably 2 to 20 carbon atoms, and most preferably 2 to 12 carbon atoms, e.g., methoxycarbonylamino), an aryloxycarbonylamino group (preferably an aryloxycarbonylamino group having 7 to 30 carbon atoms, more preferably 7 to 20 carbon atoms, and most preferably 7 to 12 carbon atoms, e.g., phenyloxycarbonylamino), a sulfonylamino group (preferably a sulfonylamino group having 1 to 30 carbon atoms, more preferably 1 to 20 carbon atoms, and most preferably 1 to 12 carbon atoms, e.g., methanesulfonylamino, benzenesulfonylamino), a sulfamoyl group (preferably a sulfamoyl group having 0 to 30 carbon atoms, more preferably 0 to 20 carbon atoms, and most preferably 0 to 12 carbon atoms, e.g., sulfamoyl, methylsulfamoyl, dimethylsulfamoyl, phenylsulfamoyl), a carbamoyl group (preferably a carbamoyl group having 1 to 30 carbon atoms, more preferably 1 to 20 carbon atoms, and most preferably 1 to 12 carbon atoms, e.g., carbamoyl, methylcarbamoyl, diethylcarbamoyl, phenylcarbamoyl), an alkylthio group (preferably an alkylthio group having 1 to 30 carbon atoms, more preferably 1 to 20 carbon atoms, and most preferably 1 to 12 carbon atoms, e.g., methylthio, ethylthio), an arylthio group (preferably an arylthio group having 6 to 30 carbon atoms, more preferably 6 to 20 carbon atoms, and most preferably 6 to 12 carbon atoms, e.g., phenylthio), a heteroarylthio group (preferably a heteroarylthio group having 1 to 30 carbon atoms, more preferably 1 to 20 carbon atoms, most preferably 1 to 12 carbon atoms, e.g., pyridylthio, 2-benzimidazolylthio, 2-benzoxazolylthio and 2-benzothiazolylthio), a sulfonyl group (preferably a sulfonyl group having 1 to 30 carbon atoms, more preferably 1 to 20 carbon atoms, and most preferably 1 to 12 carbon atoms, e.g., mesyl, tosyl), a sulfinyl group (preferably a sulfinyl group having 1 to 30 carbon atoms, more preferably 1 to 20 carbon atoms, and most preferably 1 to 12 carbon atoms, e.g., methanesulfinyl, benzenesulfinyl), a ureido group (preferably a ureido group having 1 to 30 carbon atoms, more preferably 1 to 20 carbon atoms, and most preferably 1 to 12 carbon atoms, e.g., ureido, methylureido, phenylureido), a phosphoric acid amido group (preferably a phosphoric acid amido group having 1 to 30 carbon atoms, more preferably 1 to 20 carbon atoms, and most preferably 1 to 12 carbon atoms,. e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, and a heterocyclic group (preferably a heterocyclic group having 1 to 30 carbon atoms, and more preferably 1 to 12 carbon atoms; as hetero atoms, e.g., nitrogen, oxygen, sulfur, and specifically, e.g., imidazolyl, pyridyl, quinolyl, furyl, thienyl, piperidyl, morpholino, benzoxazolyl, benzimidazolyl, benzothiazolyl, , carbazolyl, azevinyl), a silyl group (preferably a silyl group having 3 to 40 carbon atoms, more preferably 3 to 30 carbon atoms, most preferably 3 to 24 carbon atoms, e.g., trimethylsilyl, triphenylsilyl). These substituents may further be substituted.

The substituent which $R^{11}$ and $R^{12}$ each have is preferably an alkyl group or aryl group, more preferably an aryl group, even more preferably a phenyl group, and most preferably $R^{11}$ and $R^{12}$ each have no substituent.

$Ar^{11}$ and $Ar^{12}$, which may be the same or different, are represented by formula (2).

The following describes the group represented by formula (2).

$Ar^{21}$ represents an arylene or heteroarylene group. $Ar^{21}$ is preferably a phenylene, biphenylene, naphthylene, anthranylene, or pyridylene group, more preferably a phenylene or biphenylene group, and most preferably a p-phenylene group.

$Ar^{21}$ may have a substituent, and examples of the substituent are the same as the substituents A of $R^{11}$ and $R^{12}$, and preferable examples thereof are also the same as those of $R^{11}$ and $R^{12}$, and most preferably $Ar^{21}$ has no substituent.

$R^{21}$, $R^{22}$, $R^{23}$, and $R^{24}$ each independently represent a substituent or a hydrogen atom. Examples of the substituent are the same as the substituents A of $R^{11}$ and $R^{12}$; preferably an alkyl, aryl, heteroaryl group, or a substituent bonding with each other to form an aromatic ring; more preferably an aryl group or a substituent bonding each other to form an aromatic ring; and most preferably a substituent bonding each other to form an aromatic ring.

$L^2$ represents substituted or unsubstituted o-arylene, vinylene, —NR—, —O—, or —S—. R in —NR— represents a substituent of which examples are the same as those of the above-mentioned substituents A.

$L^2$ is preferably substituted or unsubstituted o-arylene, vinylene, or —NR—; more preferably unsubstituted o-arylene or vinylene; and most preferably unsubstituted o-phenylene.

m is 0 or 1, preferably 0. When m is 0, the carbon atoms to which $R^{22}$ and $R^{23}$ are bonded are linked to each other.

Examples of the compound of the present invention are shown below, but the invention is not limited to these.

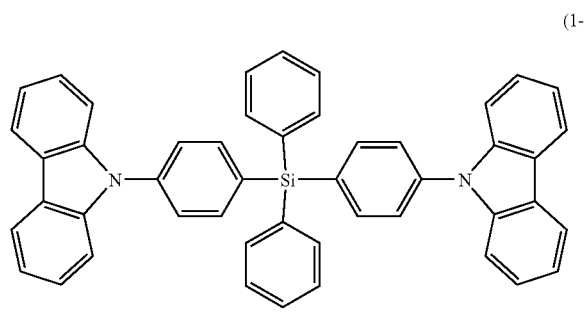

(1-1)

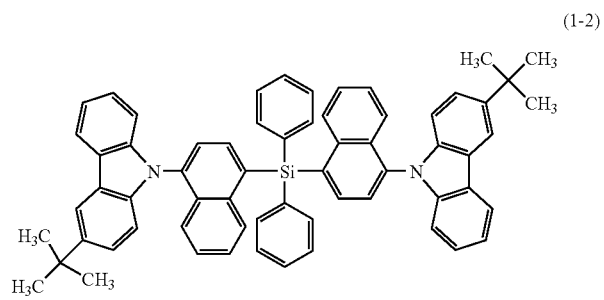

(1-2)

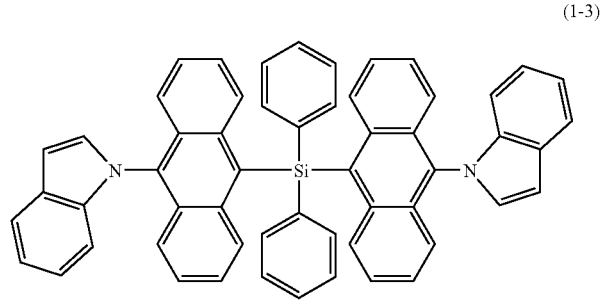

(1-3)

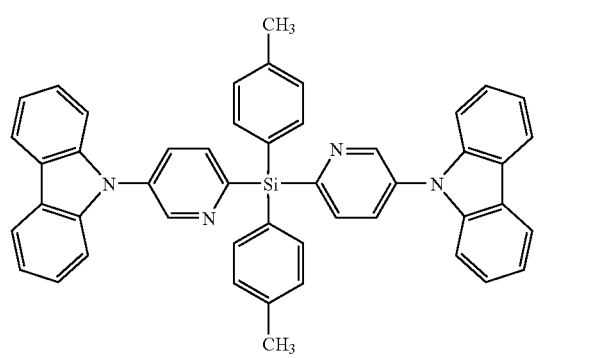

(1-4)

-continued
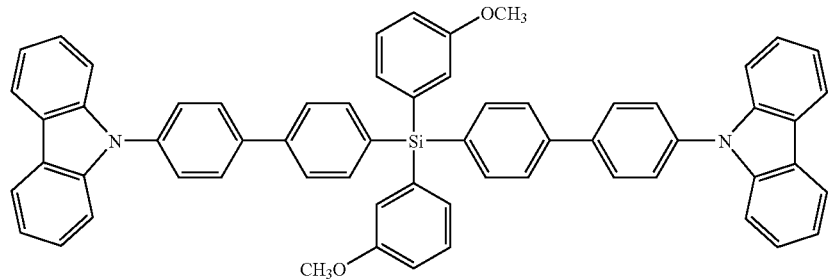
(1-5)
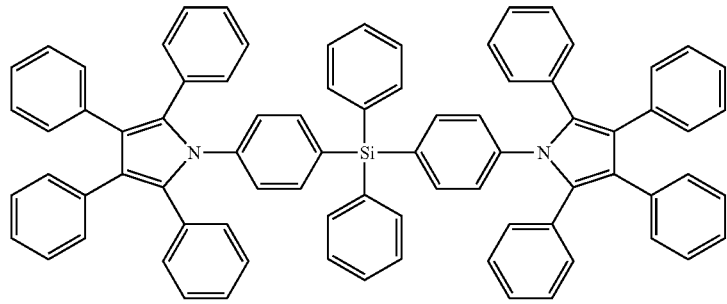
(1-6)
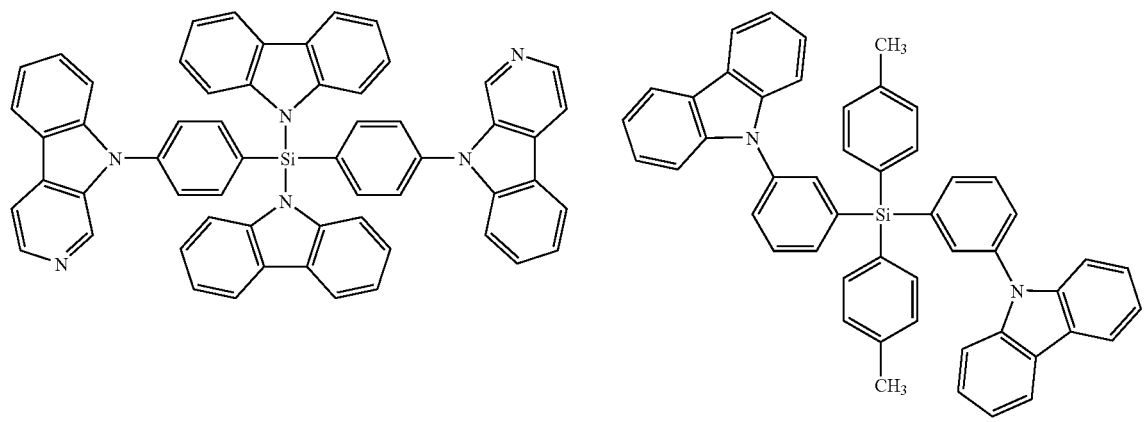
(1-7) (1-8)
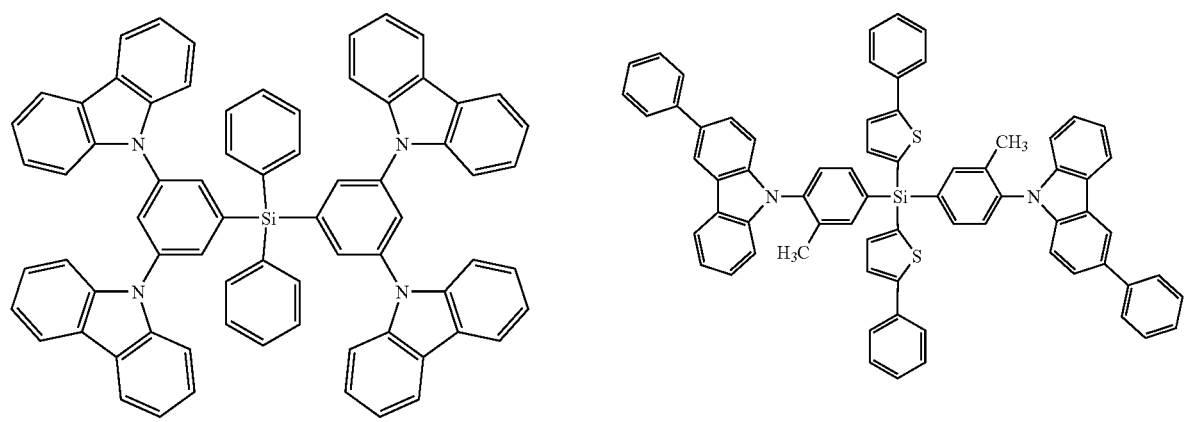
(1-9) (1-10)

(1-11)
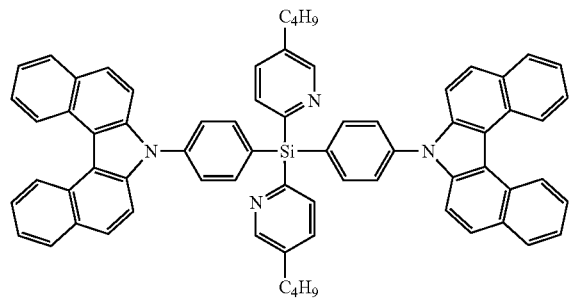
(2-1)
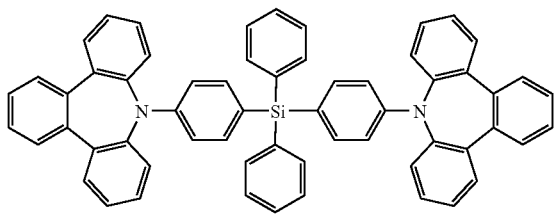
(2-2)
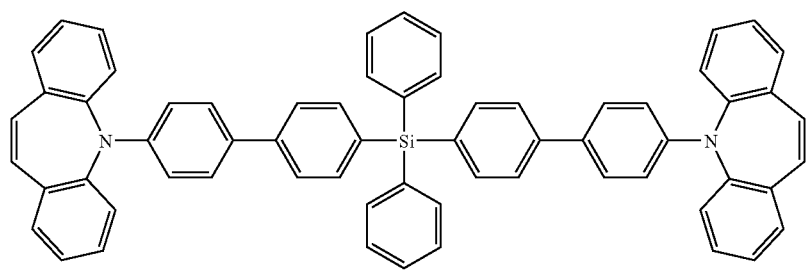
(2-3)
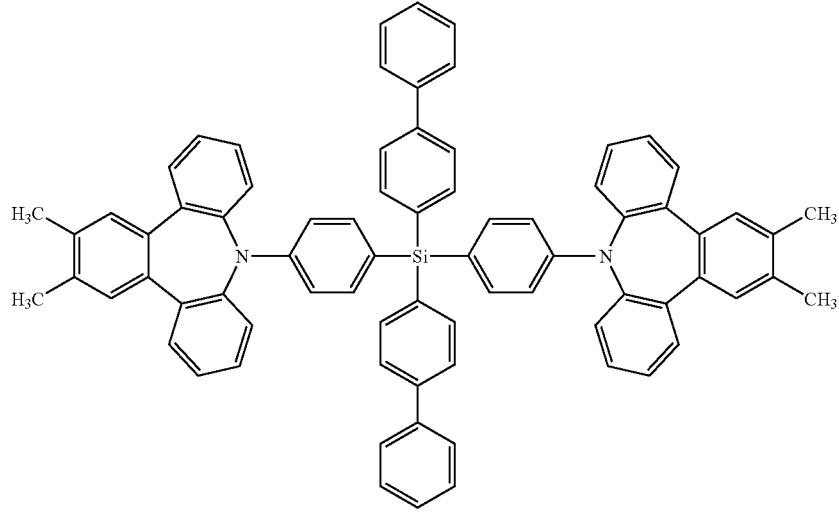
(2-4)
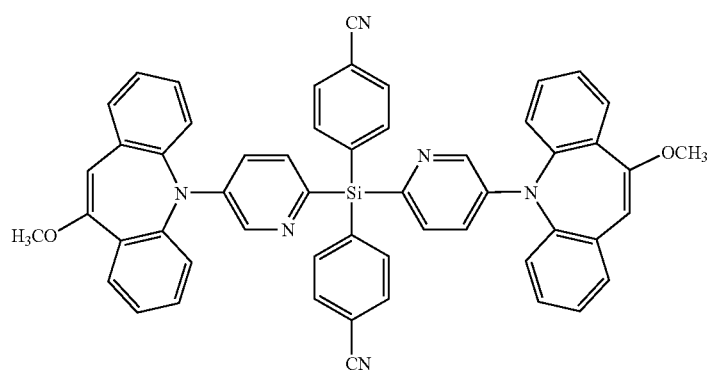

(2-5)
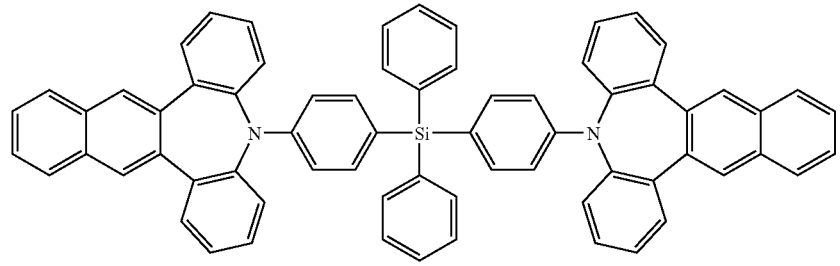
(2-6)
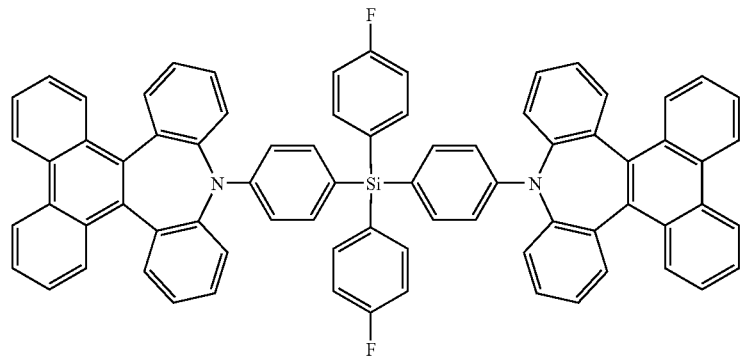
(2-7)
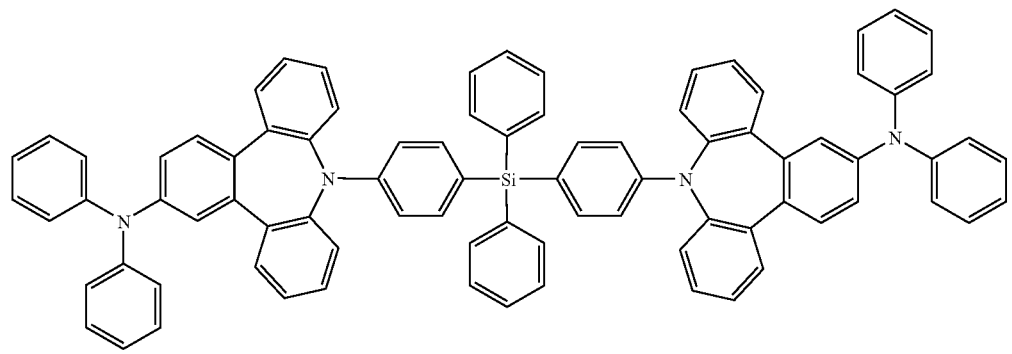
(2-8)
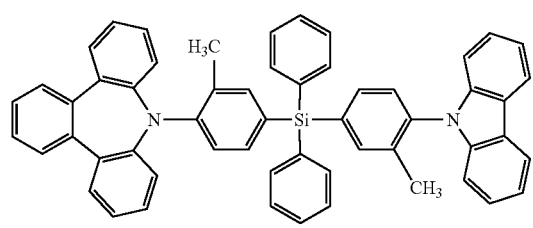
(2-9)
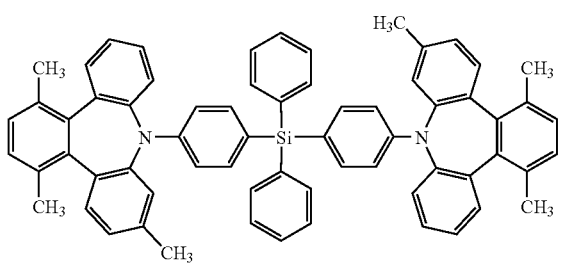

-continued
(2-10)
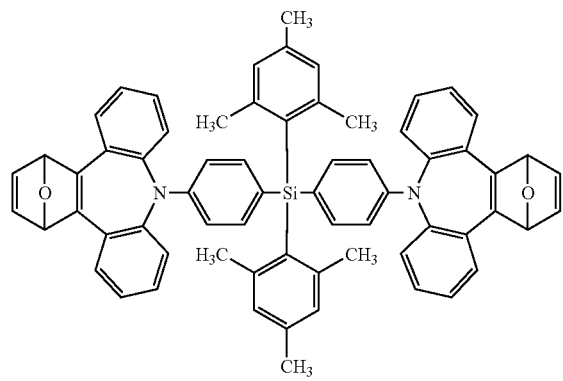
(2-11)
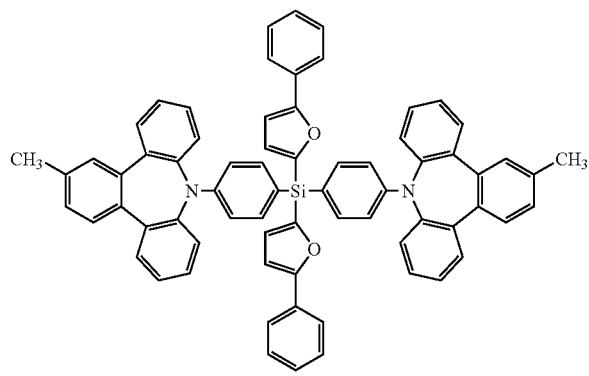
(3-1)
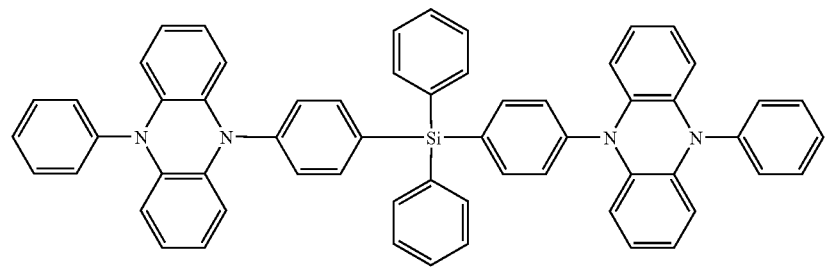
(3-2)
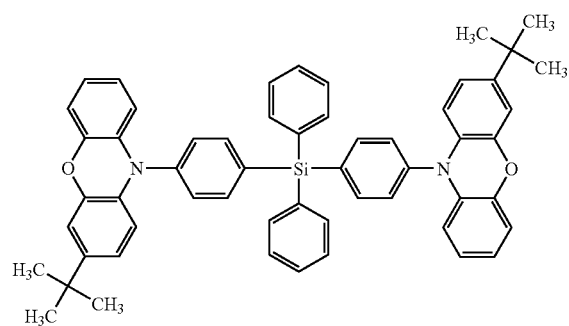
(3-3)
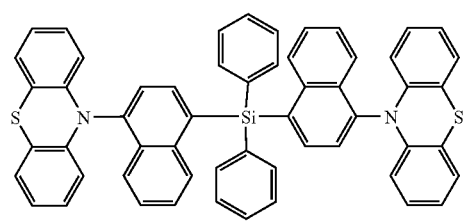
(3-4)
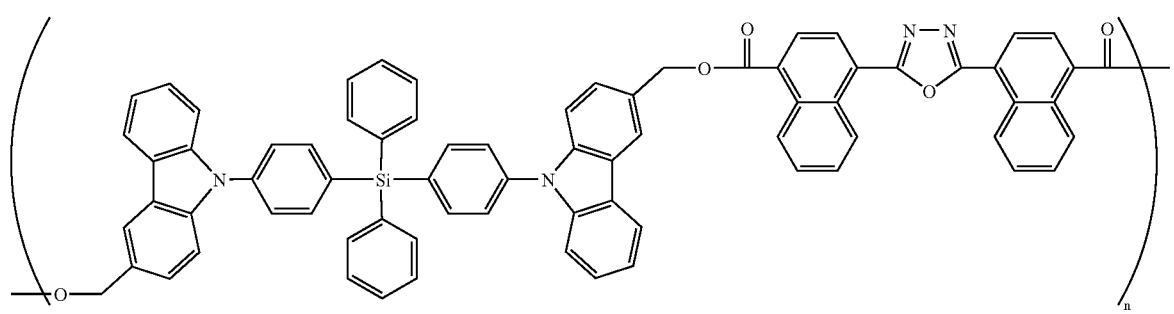

-continued (3-5)

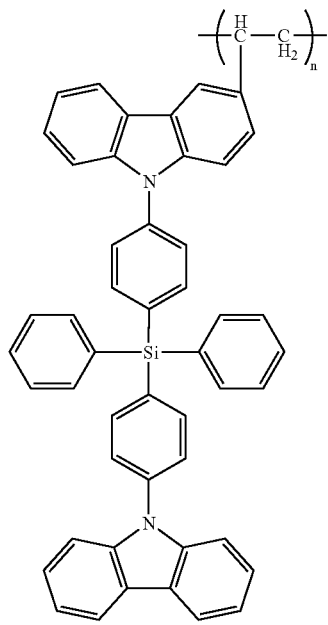

Another preferred embodiment of the present invention is a compound represented by formula (3) or (4).

formula (3)

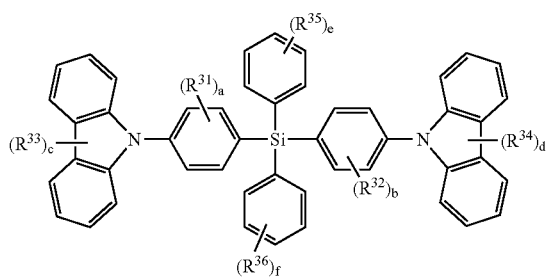

formula (4)

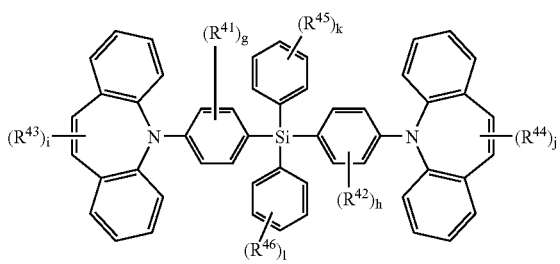

In formula (3) $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represent an alkyl group, an aryl group, or a substituent bonding with each other to form an aromatic ring; a, b, g, and h each independently represent an integer of from 0 to 4; c and d each independently represent an integer of from 0 to 8; i and j each independently represent an integer of from 0 to 2; and e, f, k, and l each independently represent an integer of from 0 to 5.

Formula (3) is explained hereinafter. In formula (3), $R^{31}$, $R^{32}$, $R^{33}$, $R^{34}$, $R^{35}$, and $R^{36}$ each independently represent an alkyl group, an aryl group, or a substituent bonding with each other to form an aromatic ring. $R^{31}$, $R^{32}$, $R^{33}$, $R^{34}$, $R^{35}$ and $R^{36}$ are each preferably an aryl group; more preferably a phenyl, naphthyl, or biphenyl group; most preferably a phenyl group.

a and b each independently represent an integer of 0 to 4, more preferably an integer of 0 to 2, even more preferably 0 or 1, and most preferably 0.

c and d each independently represent an integer of 0 to 8, preferably an integer of 0 to 6, even more preferably an integer of 0 to 4, and most preferably 0. e and f each independently represent an integer of 0 to 5, preferably an integer of 0 to 3, even more preferably 0 or 1, and most preferably 0.

The following describes formula (4). In formula (4), $R^{41}$, $R^{42}$, $R^{45}$, and $R^{46}$ each independently represent an alkyl group, an aryl group, or a substituent bonding each other to form an aromatic ring (i.e. groups which are bonded to each other to form an aromatic ring). Preferable examples thereof are the same as those of $R^{31}$, $R^{32}$, $R^{33}$, $R^{34}$, $R^{35}$, and $R^{36}$.

$R^{43}$ and $R^{44}$ each independently represent an alkyl, an aryl group, or a substituent bonding with each other to form an aromatic ring. Examples of the substituents are the same as those of $R^{31}$, $R^{32}$, $R^{33}$, $R^{34}$, $R^{35}$, or $R^{36}$; preferably an aryl group, or a substituent bonding with each other to form an aromatic ring; more preferably an aryl group or a substituent bonding with each other to form an aromatic ring; most preferably a substituent bonding with each other to form an aromatic ring.

g and h each independently represent an integer of 0 to 4, preferably an integer of 0 to 2, more preferably 0 or 1, and most preferably 0. i and j each independently represent an integer of 0 to 2, preferably 1 or 2, and most preferably 2. k and l each independently represent an integer of 0 to 5, preferably an integer of 0 to 3, more preferably 0 or 1, and most preferably 0.

Examples of the compound represented by formula (3) include compounds (1-1) and (1-2) among the above-mentioned compound examples. Examples of the compound represented by formula (4) include compounds (2-1), (2-3), (2-5), (2-6), (2-7), (2-9) and (2-10). In the present invention, however, the compound represented by formula (3) or (4) is not limited to these examples.

The process for producing the compound of the present invention is described hereinafter. The compounds represented by formula (3) or (4) can be synthesized in accordance with, for example, the following scheme:

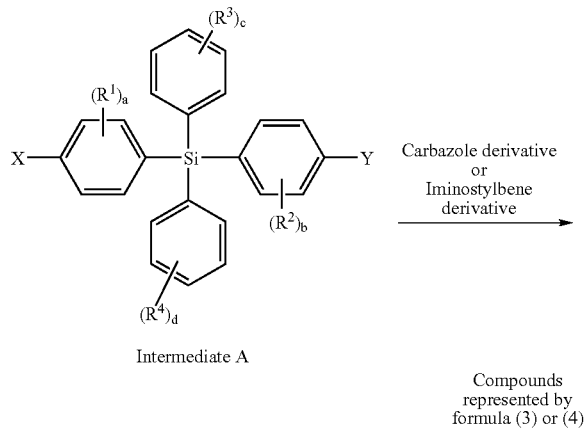

Intermediate A

Compounds represented by formula (3) or (4)

Carbazole derivative or Iminostylbene derivative wherein X and Y each independently represent a halogen atom; $R^1$, $R^2$, $R^3$, and $R^4$ each independently represent an alkyl group, an aryl group, or a substituent bonding with each other to form an aromatic ring; a and b each independently represent an integer of 0 to 4; and c and d each independently represent an integer of 0 to 5.

The intermediate A in the scheme can be synthesized by use of various known carbon-silicon bond forming reactions. The method therefor is not particularly limited. The intermediate A can be synthesized by, for example, a method described in "The Chemistry of Organic Silicon Compounds, part 1" (John Wiley & Sons), pp. 655-761 or some other document.

The compound represented by formula (3) or (4) can be synthesized from the intermediate A by use of various known carbon-nitrogen bond forming reactions. The method therefor is not particularly limited, and is preferably, for example, a synthesizing method using a palladium catalyst, as described in "Journal of American Chemical Society", 118, 7215 (1996), "Journal of American Chemical Society", 118, 7217 (1996), or some other document.

Examples of the palladium catalysts include, but are not limited to, palladium tetrakis(triphenylphosphine), palladium-carbon, palladium acetate, and palladium dichloride (dppf) (dppf: 1,1'-bisdiphenylphosphinoferrocene). Ligands such as triphenylphosphine and P(t-Bu)3 may be added at the same time.

In the present reaction, it is preferable to use a base. The kind of the base is not particularly limited, and examples thereof include sodium carbonate, sodium acetate, potassium carbonate, rubidium carbonate, triethylamine, sodium t-butoxide, and potassium t-butoxide. The amount of the base is not particularly limited, and is preferably from 0.1 to 20 equivalents, more preferably from 1 to 10 equivalents per equivalent of carbazole or a derivative thereof, or iminostylbene or a derivative thereof.

In this reaction, solvents are preferably used. Examples of the solvents used include, but are not limited to, ethanol, water, ethylene glycol dimethyl ether, diethylene glycol dimethyl ether, dimethylformamide, toluene, tetrahydrofuran, xylene, mesitylene, and mixed solvents thereof.

The reaction temperature when the compound of the invention is synthesized is not particularly limited, but is preferably from 20 to 220° C., more preferably from 20 to 180° C., and most preferably from 20 to 160° C.

The compound represented by any one of formula (1), (3), or (4) (hereinafter also referred to as the compound according to the present invention) may be a low molecular compound, or a oligomer, polymer compound (weight average molecular weight (converted to polystyrene) of which is preferably from 1,000 to 5,000,000, more preferably from 2,000 to 1,000,000, most preferably from 3,000 to 100,000). In case of a polymer compound, the structure represented by formula (1), (2), (3), or (4) may be present in the main chain or in the side chains of the polymer. Further, in case of a polymer compound, the compound may be a homopolymer or copolymer compound. The compound according to the present invention is preferably a low molecular compound.

The luminescence element (hereinafter referred to also as a light emitting element) of the present invention will be described. The light emitting element of the present invention is not particularly limited with respect to the system, driving method, and utilization form so far as it is an element utilizing the compound according to the invention. Light emitting elements, as representative, include organic-EL (electroluminescent) elements.

In the luminescence element of the present invention, the effect of the compound of the present invention or the layer containing the compound is not particularly limited. The compound is contained preferably in a hole transporting layer or a luminescent layer, and more preferably in a luminescent layer. Most preferably, the compound is contained as a host material in a luminescent layer.

In the luminescence element of the present invention, the compound of the invention is contained preferably as a main component in one or more organic layers. In case that one compound of the present invention is contained in a hole transporting layer, one compound or a plurality of compounds of the present invention are preferably contained. A compound that is not any compound of the present invention may also be incorporated into the layer.

On the other hand, in case that the compound of the present invention is contained in a luminescent layer, in respect to the ratio by weight between the luminescent material and the compound of the present invention, the luminescent material contained in the whole of this layer is preferably from 0.01 to 20% by weight, more preferably from 0.1 to 15% by weight, and most preferably from 0.5 to 10% by weight.

The luminescent material contained in the luminescence element of the present invention may be a fluorescence emitting compound, which emits light from its singlet excitons, or a phosphorescence emitting compound, which emits light from its triplet excitons. Examples of the luminescent material include benzoxazole and derivatives thereof, benzimidazole and derivatives thereof, benzthiazole and derivatives thereof, styrylbenzene and derivatives thereof, polyphenyl and derivatives thereof, diphenylbutadiene and derivatives thereof, tetraphenylbutadiene and derivatives thereof, naphthalimide and derivatives thereof, coumalin and derivatives thereof, condensed aromatic compounds, perynone and derivatives thereof, oxadiazole and derivatives thereof, oxazine and derivatives thereof, aldazine and derivatives thereof, pyralidine and derivatives thereof, cyclopentadiene and derivatives thereof, bisstyrylanthracene and derivatives thereof, quinacridon and derivatives thereof, pyrrolopyridine and derivatives thereof, thiadiazolopyridine and derivatives thereof, cyclopentadiene and derivatives thereof, styrylamine and derivatives thereof, diketopyrrolopyrole and derivatives thereof, aromatic dimethylidene and derivatives thereof, various metal complexes, typical examples of which include metal complexes of 8-quinolinol and derivatives thereof, metal complexes of pyrromethene and derivatives thereof, rare earth element complexes, and transition metal complexes; polymer compounds such as polythiophene, polyphenylene, and polyphenylenevinylene; and organic silane compounds and derivatives thereof. The luminescent material is preferably selected from condensed aromatic compounds, quinacridon and derivatives thereof, diketopyrrolopyrrole and derivatives thereof, metal complexes of pyrromethene and derivatives thereof, rare earth element complexes, and transition metal complexes, and is more preferably selected from condensed aromatic compounds and transition metal complexes.

In case that the luminescent material is a phosphorescence emitting compound, which emits light from its triplet excitons, the luminescent material is in particular preferably a transition metal complex. The central metal of the transition metal complex is not particularly limited, but is preferably iridium, platinum, rhenium, or ruthenium, more preferably iridium or platinum, most preferably iridium. Of the transition metal complexes, orthometalated complexes are preferred. The term "orthometalated complex" is a general term for a group of compounds described in "Yuki Kinzoku, Kiso To Oyo", written by Akio Yamamoto and published by Shokabo Sha in 1982, p. 150 and p. 232; and "Photochemistry and Photophysics of Coordination Compound" written by H. Yersin and published by Springer-Verlag in 1987, pp. 71 to 77 and pp. 135 to 146.

The phosphorescence material has a phosphorescence quantum yield at 20° C. or higher of preferably 70% or more, more preferably 80% or more, most preferably 85% or more.

As the phosphorescence-emitting material, there may be utilized, for example, those described in patent literature such as U.S. Pat. No. 6,303,231 B1, U.S. Pat. No. 6,097,147, WO 00/57676, WO 00/70655, WO 01/08230, WO 01/39234 A2, WO 01/41512 A1, WO 02/02714 A2, WO 02/15645 A1, JP-A-2001-247859, Japanese Patent Application No. 2000-33561, Japanese Patent Application No. 2001-189539, Japanese Patent Application No. 2001-248165, Japanese Patent Application No. 2001-33684, Japanese Patent Application No. 2001-239281, Japanese Patent Application No. 2001-219909, EP 1211257, JP-A-2002-226495, JP-A-2002-234894, JP-A-2001-247859, JP-A-2001-298470, JP-A-2002-173674, JP-A-2002-203678, JP-A-2002-203679; and non-patent literature such as Nature, vol. 395, p. 151 (1998), Applied Physics Letters, vol. 75, p. 4 (1999), Polymer Preprints, vol. 41, p. 770 (2000), Journal of American Chemical Society, vol. 123, p. 4304 (2001), Applied Physics Letters, vol. 79, p. 2082 (1999).

The formation method of the organic layer (organic compound layer) of the light emitting element containing the compound of the present invention is not particularly limited but includes resistance heating vapor deposition, electron beam irradiation, sputtering, molecular lamination method, coating methods, inkjet method, printing method, and transfer method. Above all, resistance heating vapor deposition, coating method, transfer method, and the like are preferable from the standpoints of characteristics and manufacture.

The light emitting element of the present invention may be an element in which at least one organic compound film including a light emitting layer is formed between a pair of electrodes, an anode and a cathode, and may further have a hole injection layer, a hole transporting layer, an electron injection layer, an electron transporting layer, a protective layer, and the like, in addition to the light emitting layer. Each of these layers may be provided with another function. Various materials may be used for the formation of the respective layers.

Examples of the substrate material of the light-emitting element of the present invention, is not particularly limited, include inorganic materials such as zirconia-stabilized yttrium, glass and the like; and macromolecular (high molecular) materials such as polyesters (for example, polyethylene terephthalate, polybutylene terephthalate, and polyethylene naphthalate), polyethylenes, polycarbonates, polyethersulfones, polyarylates, allyldiglycolcarbonates, polyimides, polycycloolefins, norbornene resins, poly(chlorotrifluoroethylene), Teflon (registered trade mark), and polytetrafluoroethylene-polyethylene copolymer, and the like.

The anodes, supplying holes to the hole injection layers, the hole transporting layers, the light emitting layers, and the like, may be formed of metals, alloys, metal oxides, electric conductive compounds, mixtures thereof, and the like, preferably materials having a work function of 4 eV or more. Examples thereof include conductive metal oxides such as tin oxide, zinc oxide, indium oxide, indium tin oxide (ITO), and the like; metals such as gold, silver, chromium, nickel, and the like; further mixtures or laminates of the metals with the conductive metal oxides; inorganic conductive materials such as copper iodide, copper sulfide, and the like; organic conductive materials such as polyaniline, polythiophene, polypyrrole, and the like; and laminates thereof with ITO. Conductive metal oxides are prefered, and ITO is particularly preferred in terms of productivity, high conductivity, and transparency. The thickness of the anode may be appropriately selected depending on the kind of material, preferably from 10 nm to 5 μm, more preferably from 50 nm to 1 μm, and most preferably from 100 nm to 500 nm.

As the anode, one in which layer formation is carried out on soda-lime glass, non-alkali glass, or a transparent resin substrate is usually used. When glass is used, non-alkali glass is preferably used for decreasing ions eluted from glass. When soda lime-glass is used, it is preferable to use one provided with a barrier coat of silica or the like. There is no particular limitation on the thickness of the substrate, as long as it is sufficient to keep its mechanical strength. When glass is used, the thickness is usually 0.2 mm or more, and preferably 0.7 mm or more.

Various methods are used for the preparation of the anodes depending on the kind of material. For example, in case of ITO, film formation may be carried out by methods such as electron beam processing, sputtering, resistance heating vapor deposition, chemical reaction (sol-gel processing), coating of a dispersion of ITO, and the like.

According to treatments of the anode such as washing and others, the driving voltage for the light emitting element may be reduced and the luminance efficiency may be raised. For example, in a case of ITO, UV-ozone treatment and plasma treatment are effective.

The cathodes supply electrons to the electron injection layers, the electron transporting layers, the light emitting layers, and the like. The cathodes may be selected considering ionization potential, stability, and adhesion to layers adjacent to the negative electrodes, such as the electron injection layers, the electron transporting layers, and the light emitting layers. As materials for the cathodes, metals, alloys, metal oxides, electric conductive compounds, or mixtures thereof may be used. Examples thereof include alkali metals (for example, Li, Na, K) or fluorides and oxides thereof, alkali earth metals (for example, Mg and Ca) or fluorides and oxides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and ytterbium. Materials having a work function of 4 eV or less are preferred, more preferably aluminum, lithium-aluminum alloys, mixed metals thereof, magnesium-silver alloys or mixed metals thereof, or the like. The cathode may have a single layer structure of the compounds and the mixture, or an accumulated layer structure containing the compounds and the mixtures. For example, accumulated layer structures of aluminum/lithium fluoride and aluminum/lithium oxide are preferable. The film thickness of the cathode can be appropriately selected depending on the material, and is preferably from 10 nm to 5 µm, more preferably from 50 nm to 1 µm, and further preferably from 100 nm to 1 µm.

For the preparation of the cathodes, methods such as electron beam processing, sputtering, resistance heating vapor deposition, and coating are used. The metals may be vapor deposited as simple substances, or two or more components may be vapor deposited at the same time. Further, it is also possible to vapor deposit a plurality of metals at the same time to form an alloy electrode, or an alloy previously prepared may also vapor deposited.

The anodes and the cathodes with low sheet resistance are preferable, and those with several-hundred Ω/□ or less are preferable.

Materials for the luminescent layer (hereinafter referred to also as light emitting layer) may be any, as long as they can form layers having the function of being able to inject, upon electric field application, holes from the anodes, the hole injection layers, or the hole transporting layers, and inject electrons from the cathodes, the electron injection layers, or the electron transporting layers; the function of transporting injected charges; or the function of providing the field of recombination of holes with electrons to emit light. Examples include benzoxazole, benzimidazole, benzthiazole, styrylbenzene, polyphenyl, diphenylbutadiene, tetraphenylbutadiene, naphthalimide, coumarin, perylene, perynone, oxadiazole, aldazine, pyrazine, cyclopentadiene, bis(styryl)anthracene, quinacridone, pyrrolopyridine, thiadiazolopyridine, cyclopentadiene, styrylamine, aromatic dimethylidyne compounds, various metal complexes represented by metal complexes or rare earth element complex of 8-quinolinol, and polymers such as polythiophene, polyphenylene, polyphenylenevinylene, organic silane compounds, tris(phenylpyridine)iridium complex, transition metal complexes represented by porphyrin platinum complexes, the derivatives thereof, and the like. The light emitting layers include at least a phosphorescence material. Although there is no particular limitation on the thickness of the light emitting layer, it is usually preferably from 1 nm to 5 µm, more preferably from 5 nm to 1 µm, and most preferably from 10 nm to 500 nm.

Although there is no particular limitation on methods for forming the light emitting layers, methods such as resistance heating vapor deposition, electron beam processing, sputtering, molecular lamination, coating (spin coating, casting and dip coating), inkjet process, printing and LB processing are used. Preferred are resistance heating vapor deposition and coating.

The luminescent layer may be made of a single compound or plural compounds. As well as the luminescent layer, which is a single layer, plural luminescent layers may be used. The layers may emit rays in different colors, so as to emit, for example, a white ray, or the single luminescent layer may emit a white ray. In case of the plural luminescent layers, each of the luminescent layers may be made of a single material or plural compounds.

The luminescent layer of the organic electroluminescence element of the present invention may have at least one layered structure. The number of layers in this structure is preferably from 2 to 50, more preferably from 4 to 30, and most preferably from 6 to 20.

The thickness of each of the layers constituting the layered structure is not particularly limited, but it is preferably from 0.2 to 20 nm, more preferably from 0.4 to 15 nm, even more preferably from 0.5 to 10 nm, and most preferably from 1 to 5 nm.

The luminescent layer of the organic electroluminescence element of the invention may have plural domain structures. The luminescent layer may contain therein some other domain structure. The diameter of each of the domain structures is preferably from 0.2 to 10 nm, more preferably from 0.3 to 5 nm, even more preferably from 0.5 to 3 nm, and most preferably from 0.7 to 2 nm.

Materials for the hole injection layers and the hole transporting layers may be any, as long as they have any of the function of injecting holes from the anodes, the function of transporting holes, and the function of blocking electrons injected from the cathodes. Examples thereof include carbazole, triazole, oxazole, oxadiazole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, aromatic dimethylidyne compounds, polyphiline compounds, polysilane compounds, poly(N-vinylcarbazole), aniline copolymers, conductive high molecular oligomers such as thiophene oligomers and polythiophene, organic silane derivatives, carbon film, and the compounds of the present invention, and the derivatives thereof, and the like. Although there is no particular limitation of the thickness of the hole injection layer and the hole transporting layer, it is usually preferably from 1 nm to 5 µm, more preferably from 5 nm to 1 µm, and most preferably from 10 nm to 500 nm. The hole injection layer and the hole transporting layer may have either a monolayer structure comprising one or more kinds of the above-mentioned materials, or a multilayer (accumulated layer) structure having a plurality of layers each comprising the same composition or different compositions.

As methods for forming the hole injection layers and the hole transporting layers, vacuum deposition, LB processing, coating (spin coating, casting and dip coating) of the above-mentioned materials for the hole injection layers and the hole transporting layers dissolved or dispersed in solvents, inkjet process, printing, and transfer method are used. In case of coating, the materials may be dissolved or dispersed together with resin components. .The resin components include, for example, polyvinyl chloride, polycarbonates, polystyrene, polymethyl methacrylate, polybutyl methacrylate, polyesters, polysulfones, polyphenylene oxide, polybutadiene, poly(N-vinylcarbazole), hydrocarbon resins, ketone resins, phenoxy resins, polyamides, ethyl cellulose, vinyl acetate, ABS resins, polyurethane, melamine resins, unsaturated polyester resins, alkyd resins, epoxy resins and silicone resins.

Materials for the electron injection layers and the electron transporting layers may be any, as long as they have any of the function of injecting electrons from the cathodes, the function of transporting electrons, and the function of blocking holes injected from the anodes. Examples thereof include triazole, oxazole, oxadiazole, imidazole, fluorenone, anthraquinodimethane, anthrone, diphenylquinone, thiopyran dioxide, carbodiimide, fluorenylidenemethane, distyrylpyrazine, naphthalene, tetracarboxylic acid anhydrides of aromatic condensed rings such as naphthalene and perylene; phthalocyanine, various metal complexes represented by metal complexes of 8-quinolinol, metallophthalocyanine, and metal complexes each having benzoxazole or benzothiazole as a ligand, organic silane, the compounds of the invention, and the derivatives thereof. Although there is no particular limitation of the thickness of the electron injection layer and the electron transporting layer, it is usually preferably from 1 nm to 5 μm, more preferably from 5 nm to 1 μm, and most preferably from 10 nm to 500 nm. The electron injection layer and the electron transporting layer may have either a monolayer structure comprising one kind or two or more kinds of the above-mentioned materials, or a multilayer (an accumulated layer) structure having a plurality of layers each comprising the same composition or different compositions.

As methods for forming the electron injection layers and the electron transporting layers, vacuum deposition, LB processing, coating (spin coating, casting and dip coating) of the above-mentioned materials for the hole injection layers and the hole transporting layers dissolved or dispersed in solvents), inkjet process, printing, transfer are used. In case of coating, the materials can be dissolved or dispersed together with resin components. As the resin components, for example, ones illustrated in the case of the hole injection layers and the hole transporting layers can be applied.

Materials for the protective layers may be any, as long as they have the function of inhibiting promoters of element deterioration such as water and oxygen from entering the elements. Examples thereof include metals such as In, Sn, Pb, Au, Cu, Ag, Al, Ti, and Ni, metal oxides such as MgO, SiO, $SiO_2$, $Al_2O_3$, GeO, NiO, CaO, BaO, $Fe_2O_3$, $Y_2O_3$, and $TiO_2$, metal fluorides such as $MgF_2$, LiF, $AlF_3$, and $CaF_2$, nitrides such as $SiN_x$ and $SiO_xN_y$; polyethylene, polypropylene, polymethyl methacrylate, polyimides, polyureas, polytetrafluoroethylene, polychlorotrifluoroethylene, polydichlorodifluoroethylene, copolymers of chlorotrifluoroethylene and dichlorodifluoroethylene, copolymers obtained by copolymerizing monomer mixtures each containing tetrafluoroethylene and at least one kind of comonomer, fluorine-containing copolymers having cyclic structures on main chains of the copolymers, water-absorptive substances having a water absorption of 1% or more, and moisture-proof substances having a water absorption of 0.1% or less.

There is no particular limitation on methods for forming the protective layers. For example, vacuum deposition, sputtering, reactive sputtering, MBE (molecular beam epitaxy), cluster ion beam processing, ion plating, plasma polymerization (high-frequency excitation ion plating), plasma CVD, laser CVD, thermal CVD, gas source CVD, coating, inkjet process, printing, and transfer can be applied.

The light-extraction efficiency in the luminescence element of the present invention may be improved by various conventional techniques. For example, surface structuring of the substrate (for example, formation of a fine concavo-convex pattern), controlling the refractive index of the substrate, ITO layer, or organic layer(s), and controlling the thickness of the substrate, ITO layer, or organic layer(s). These improvements may lead to increase light-extraction efficiency and external quantum efficiency.

The light-emitting element of the invention may be of a so-called top emission type, in which light is emitted from the anode side of the device.

The organic electroluminescence element of the present invention and the silicon compounds therein may enhance the luminescence property, and improve its element-driving endurance and storage stability.

The present invention will be described in more detail based on examples given below, but the invention is not meant to be limited by these.

EXAMPLES

Example 1

Synthesis of Compound A-1:

Under nitrogen air flow, 20 g of 1,4-dibromobenzene and 100 ml of dehydrated diethyl ether were cooled with ice, and thereto was dropwise added 1.6 mol/l of n-butyllithium/hexane solution over 20 minutes. After the end of the addition, the ice bath was taken off, and the temperature of the solution was raised to room temperature. The solution was further stirred. After 30 minutes, the solution was again cooled with ice. Thereto was dropwise added 10.7 g of dichlorodiphenylsilane over 30 minutes. After the end of the addition, the temperature of the solution was raised to room temperature, and further the solution was continuously stirred. After 3 hours, thereto was dropwise added 90 ml of a 1.0 mol/l hydrochloric acid solution in water. After the addition, to the solution were further added 200 ml of chloroform and 100 ml of water, thereby separating the solution into two phases. The resultant organic phase was washed with water, dried with magnesium sulfate, and filtrated, and then the solvent was distilled off under reduced pressure. The resultant white solid was recrystallized from a mixed solution of chloroform an hanol, so as to yield 15.0 g of a compound A-1 (yield: 71%).

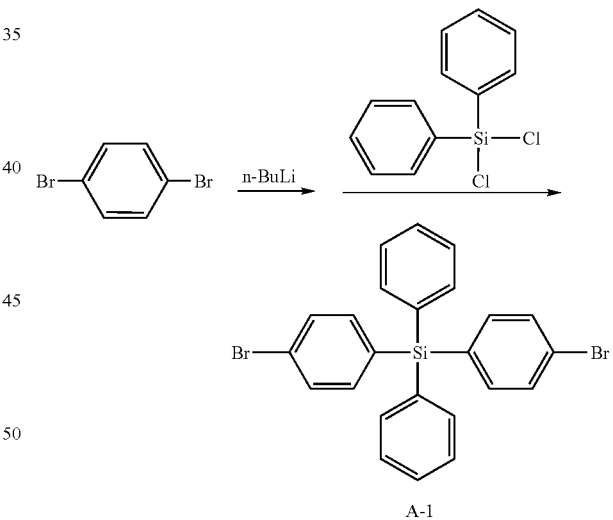

Synthesis of Exemplified Compound (1-1):

Under nitrogen air flow, 2.6 g of the compound A-1, 1.8 g of carbazole, 0.08 g of palladium biacetate, 4.1 g of rubidium carbonate, 0.24 g of tris-t-butylphosphine, and 50 ml of xylene were heated and refluxed while stirred for 3 hours. The advance of the reaction was traced by TLC (thin layer chromatography). After it was verified that the compound A vanished, 50 ml of chloroform and 50 ml of water were added to the reaction mixture to separate the solution into two phases. The resultant organic phase was dried with magnesium sulfate, and filtrated, and then solvent was distilled off under reduced pressure. The resultant solid was purified with column chromatograph (hexane/chloroform), and then recrystallized from a mixed solvent of hexane and chloroform, so as to yield 2.6 g of an exemplified compound (1-1) (yield: 75%). M.P. 274° C.

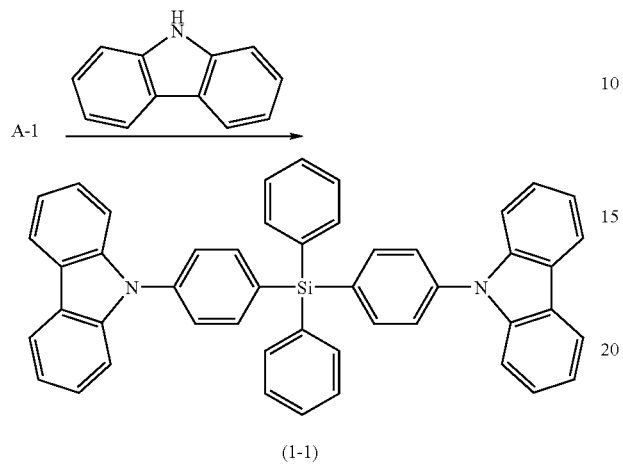

(1-1)

Example 2

Synthesis of Compound B:

A compound B illustrated below is described as an exemplified compound (1-1) in JP-A-2001-97953, and the compound was synthesized by the process described in this document.

Synthesis of Exemplified Compound (2-1):

Under nitrogen air flow, 5.0 g of the compound A-1, 5.4 g of the compound B, 0.11 g of palladium biacetate, 0.31 g of tris-t-butylphosphine, 3.9 g of sodium t-butoxide, and 100 ml of xylene were heated and refluxed while stirred for 3 hours. The advance of the reaction was traced by TLC (thin layer chromatography). After it was verified that the compound A-1 vanished, 100 ml of chloroform and 100 ml of water were added to the reaction mixture to separate the solution into two phases. The resultant organic phase was dried with magnesium sulfate, and filtrated, and then solvent was distilled off under reduced pressure. The resultant solid was purified with column chromatograph (hexane/chloroform), and then recrystallized from a mixed solvent of hexane and chloroform, so as to yield 4.8 g of an exemplified compound (2-1) (yield: 58%). M.P. 364° C.

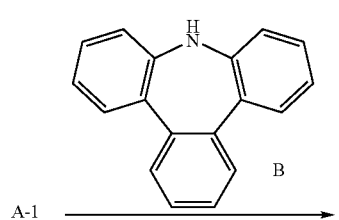

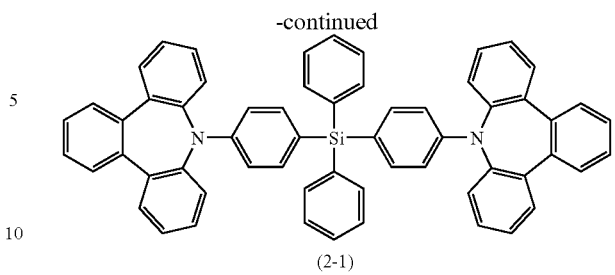

(2-1)

Example 3

Oxidation Wave Reversibility Evaluation by CV (Cyclic Voltammetry) Method:

The present example was carried out to evaluate the stability of the compound of the present invention in EL elements.

It is considered that at the time of driving an EL element, organic compound material in the element is continually oxidized or reduced by injecting, transporting charges of holes or electrons. It is therefore effective to measure the CV of the organic compound material as one method for evaluating the stability of the organic compound material when the element is driven.

In other words, when the oxidation wave or reduction wave obtained by the CV method is reversible, it can be judged that the organic compound material is stable against oxidation or reduction. In further repeated sweepings, when a change in the waveform of the resultant oxidation wave or reduction wave from the initial waveform is small, it can be judged that the material is more stable against oxidation or reduction.

In order to evaluate the oxidation stability of materials in the present example, under the following CV measuring conditions, the reversibility of the oxidation wave therefrom was evaluated, and the change of the waveform from an initial sweeping during repeated sweepings was measured.

CV measuring conditions

Supporting electrolyte: $^nBu_4N.PF_6$(0.1 M)
Working electrode: Pt
Counter electrode: Pt
Reference electrode: SCE
Sweeping speed: 100 mV/s
Measuring range: 0 to +1.6 V versus SCE A 1.0 mM solution of each of the materials in a mixed solvent of benzene and acetonitrile (1:1) was prepared as a sample solution. After the preparation of the solution, the solution was filtrated with a membrane filter, and then the resultant solution was subjected to Ar bubbling. Thereafter, the CV of the solution was measured.

The results are shown in a table described below.

TABLE 1

Reversibility of oxidation wave measured by CV method and waveform change in repeated sweepings.

| | Reversibility of oxidation wave | Waveform change in repeated sweepings |
|---|---|---|
| CBP (Comparative example) | Irreversible | Change in waveform in each repeated sweeping |
| Compound C (Comparative example) Compound described in JP-A-2000-351966 | Irreversible | Change in waveform in each repeated sweeping |

TABLE 1-continued

Reversibility of oxidation wave measured by CV method and waveform change in repeated sweepings.

| | Reversibility of oxidation wave | Waveform change in repeated sweepings |
|---|---|---|
| Compound (1-1) (This invention) | Reversible | No Change in waveform in repeated sweepings |

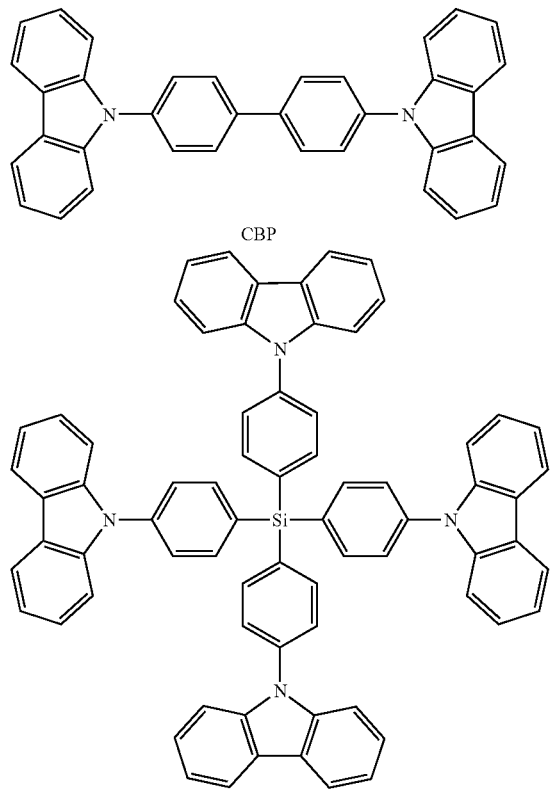

CBP

C (Compound described in JP-A-2000-351966)

As described above, it was found that the compound (1-1) of the present invention was excellent in the oxidation wave reversibility measured by the CV method, comparing with the compounds of the comparative examples, and the waveform change in the repeated sweepings was also small. The present result demonstrates that the compound of the present invention has high oxidation stability, and the result shows that any EL element formed by use of the compound of the present invention attains superior driving-endurance.

Example 4

A washed ITO substrate was put into a vapor deposition machine. First, copper phthalocyanine was vapor-deposited, as a hole injecting layer, into a thickness of 10 nm on the substrate. Thereon was vapor-deposited α-NPD (N,N'-diphenyl-N,N'-di(α-naphthyl)-benzidine), as a hole transporting layer, into a thickness of 30 nm. The exemplified compound (1-1) and Ir(ppy)$_3$ were co-vapor-deposited into a thickness of 30 nm, at a ratio (by weight) of 9/1, on the hole transporting material. Thereon were successively vapor-deposited BAlq into a thickness of 10 nm and Alq$_3$ into a thickness of 40 nm. A patterned mask (its light emitting area: 4 mm×5 mm) was set onto the organic thin film, and lithium fluoride was vapor-deposited into a thickness of about 1 nm on the organic thin film in the vapor deposition machine. Aluminum was vapor-deposited into a thickness of about 200 nm on this lithium fluoride, so as to produce an element A source measure unit 2400 model, manufactured by Toyo Corporation, was used to apply a constant DC voltage to the EL element, thereby emitting light. The luminance thereof was measured with a luminance meter BM-8 manufactured by Topcon Corporation, and the luminescence wavelength thereof was measured with a spectrum analyzer PMA-11 manufactured by Hamamatsu Photonics K.K.

As a result, green luminescence having a chromaticity value (0.27, 0.62) was obtained, and the external quantum efficiency of the element was 7.5%. The endurance of the present element was evaluated at an initial luminance of 2000 cd/m$^2$ and a constant electric current value. As a result, the half-value period of the luminance was about 800 hours.

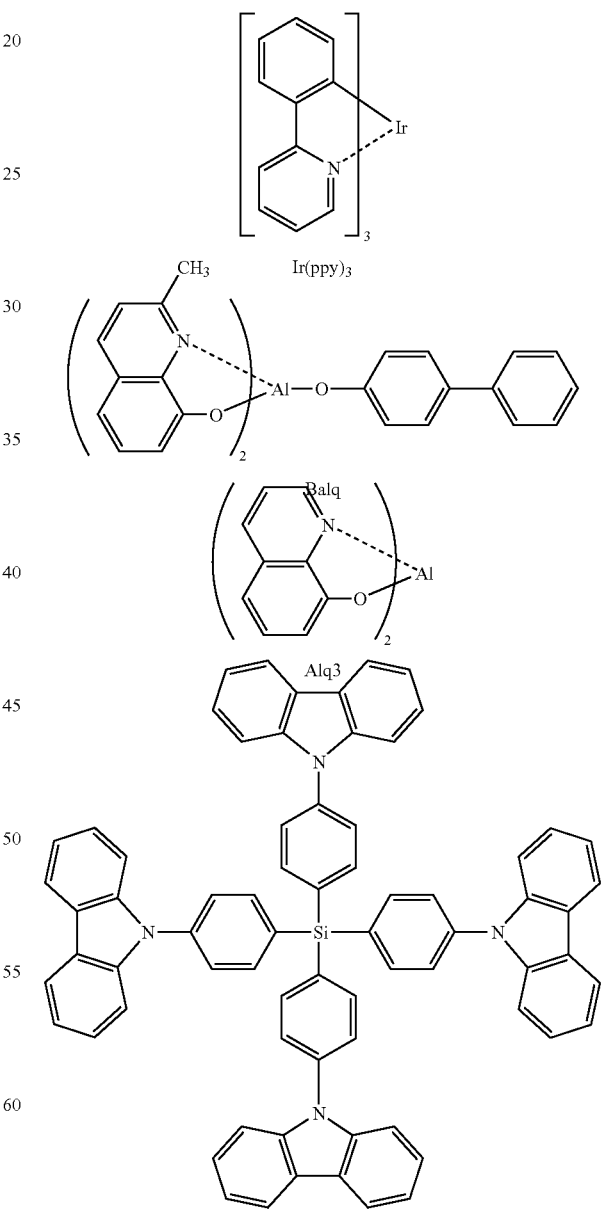

C (Compound described in JP-A-2000-351966)

Example 5

An element was formed and evaluated in the same way as in Example 4 except that the compound (2-1) was used instead of NPD and further CBP was used instead of the compound (1-1).

As a result, green luminescence having a chromaticity value (0.26, 0.61) was obtained, and the external quantum efficiency of the element was 7.2%. The endurance of the present element was evaluated at an initial luminance of 2000 cd/m² and a constant electric current value. As a result, the half-value period of the luminance was about 700 hours.

Comparative Example 1

An element was formed and evaluated in the same way as in Example 4 except that CBP was used instead of the compound (1-1).

As a result, green luminescence having a chromaticity value (0.27, 0.62) was obtained, and the external quantum efficiency of the element was 6.0%. The endurance of the present element was evaluated at an initial luminance of 2000 cd/m² and a constant electric current value. As a result, the half-value period of the luminance was about 400 hours.

Comparative Example 2

An element was formed and evaluated in the same way as in Example 4 except that the compound C described in JP-A-2000-351966 was used instead of the compound (1-1).

As a result, green luminescence having a chromaticity value (0.27, 0.62) was obtained, and the external quantum efficiency of the element was 5.0%. The endurance of the present element was evaluated at an initial luminance of 2000 cd/m² and a constant electric current value. As a result, the half-value period of the luminance was about 200 hours.

Similarly, a high-efficiency luminescence element can be produced by use of a different compound of the present invention also.

Having described our invention as related to the present embodiments, it is our intention that the invention not be limited by any of the details of the description, unless otherwise specified, but rather be construed broadly within its spirit and scope as set out in the accompanying claims.

What is claimed is:

1. An organic electroluminescence element, comprising at least one organic layer that includes a luminescent layer between a pair of electrodes, wherein said organic layer contains at least one compound represented by formula (3) or (4):

formula (3)

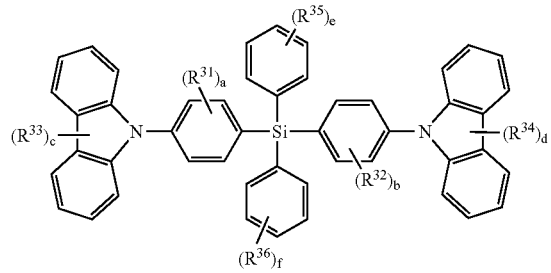

formula (4)

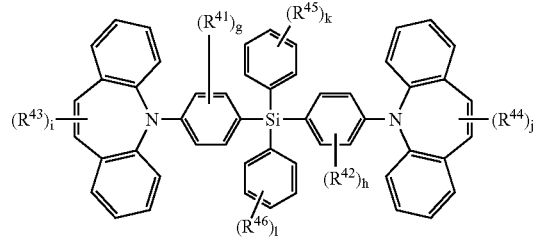

wherein $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represents an alkyl group, an aryl group, or a substituent bonding with each other to form an aromatic ring; a, b, g, and h each independently represents an integer from 0 to 4; c and d each independently represents an integer from 0 to 8; i and j each independently represents an integer from 0 to 2; and e, f, k, and l each independently represents an integer from 0 to 5.

2. The organic electroluminescence element according to claim 1, wherein in formula (3), $R^{31}$, $R^{32}$, $R^{33}$, $R^{34}$, $R^{35}$, and $R^{36}$ each independently represents an aryl group; c and d each independently represents an integer from 0 to 4; and a, b, e and f each independently represents an integer from 0 to 1.

3. The organic electroluminescence element according to claim 1, wherein in formula (4), $R^{41}$, $R^{42}$, $R^{45}$, and $R^{46}$ each independently represents an aryl group; $R^{43}$ and $R^{44}$ each independently represents a substituent bonding with each other to form an aromatic ring; i and j each independently represents an integer from 1 to 2; and g, h, k, and l each independently represents an integer from 0 to 1.

4. A compound represented by formula (3) or (4):

formula (3)

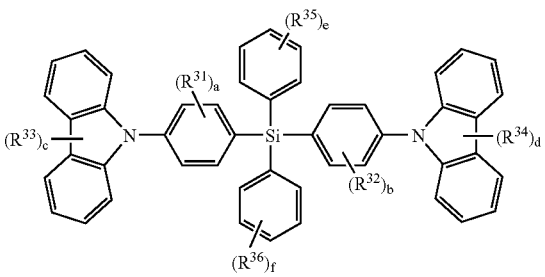

formula (4)

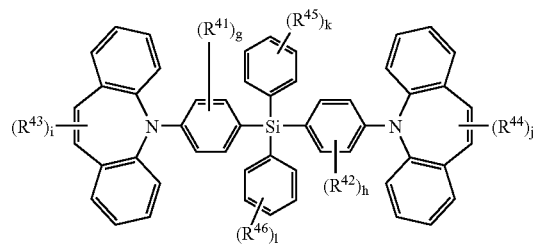

wherein $R^{31}$, $R^{32}$, $R^{33}$, $R^{34}$, $R^{35}$, $R^{36}$, $R^{41}$, $R^{42}$, $R^{43}$, $R^{44}$, $R^{45}$, and $R^{46}$ each independently represents an alkyl group, an aryl group, or a substituent bonding with each other to form an aromatic ring; a, b, g, and h each independently represents an integer from 0 to 4; c and d each independently represents an integer from 0 to 8; i and j each independently represents an integer from 0 to 2; and e, f, k, and l each independently represents an integer from 0 to 5.

5. The compound according to claim 4, wherein the compound is a compound represented by formula (3), wherein $R^{31}$, $R^{32}$, $R^{33}$, $R^{34}$, $R^{35}$, and $R^{36}$ each independently represents an aryl group; c and d each independently represents an integer from 0 to 4; and a, b, e and f each independently represents an integer from 0 to 1.

6. The compound according to claim 4, wherein the compound is a compound represented by formula (4), wherein $R^{41}$, $R^{42}$, $R^{45}$ and $R^{46}$ each independently represents an aryl group; $R^{43}$ and $R^{44}$ each independently represents a substituent bonding with each other to form an aromatic ring; i and j each independently represents an integer from 1 to 2; and g, h, k, and l each independently represents an integer from 0 to 1.

7. The organic electroluminescence element according to claim 1, wherein $R^{43}$ and $R^{44}$ each independently represents a substituent forming a condensed benzene ring; and wherein each of a, b, c, d, e, f, g, h, k, and l is 0.

* * * * *